(12) United States Patent
Lynch et al.

(10) Patent No.: US 7,894,874 B2
(45) Date of Patent: Feb. 22, 2011

(54) METHOD AND APPARATUS FOR ENHANCING THE DETECTING AND TRACKING OF MOVING OBJECTS USING ULTRASOUND

(75) Inventors: John Edward Lynch, Williamsburg, VA (US); David Mark Blaker, Roanoke, VA (US); David J. Colatosti, Blacksburg, VA (US); Richard Burton Mack, Jr., Troutville, VA (US)

(73) Assignee: Luna Innovations Incorporated, Roanoke, VA (US)

( * ) Notice: Subject to any disclaimer, the term of this patent is extended or adjusted under 35 U.S.C. 154(b) by 1325 days.

(21) Appl. No.: 11/429,432

(22) Filed: May 8, 2006

(65) Prior Publication Data

US 2010/0262009 A1  Oct. 14, 2010

(51) Int. Cl.
*A61B 5/05* (2006.01)
*A61B 8/08* (2006.01)
*A61B 8/12* (2006.01)
*A61B 8/14* (2006.01)

(52) U.S. Cl. .................. 600/407; 600/437; 600/443

(58) Field of Classification Search ............ 600/407, 600/437–461

See application file for complete search history.

(56) References Cited

U.S. PATENT DOCUMENTS

| | | | |
|---|---|---|---|
| 5,419,331 A * | 5/1995 | Parker et al. ............... | 600/454 |
| 5,441,051 A | 8/1995 | Hileman et al. | |
| 5,570,691 A | 11/1996 | Wright et al. | |
| 5,784,336 A | 7/1998 | Gopinathan et al. | |
| 6,464,643 B1 | 10/2002 | Brock-Fisher | |
| 7,542,790 B2 * | 6/2009 | Jensen et al. ............... | 600/407 |

OTHER PUBLICATIONS

Notification of Transmittal of International Preliminary Report for International Application No. PCT/US06/17654, mailed Jul. 2, 2008.

* cited by examiner

*Primary Examiner*—Brian Casler
*Assistant Examiner*—Elmer Chao
(74) *Attorney, Agent, or Firm*—Nixon & Vanderhye P.C.

(57) ABSTRACT

An ultrasonic pulse echo apparatus detects an object that is moving with respect to stationary objects. An ultrasonic transducer transmits a series of ultrasound pulses in a direction that intersects a path of the moving object. An ultrasound receiver receives a series of lines of echoes from objects in the field of view of the ultrasonic signal. Each echo line corresponds to one of the ultrasonic pulses. A signal processor processes the echo lines from the moving object. The echo lines are time shifted by different amounts and combined at different time shifts to produce different composite lines. The composite line having an optimal signal-to-noise ratio is selected. Other signal processing enhancements are performed.

31 Claims, 6 Drawing Sheets

Original Data (m = 0)

Shift for m = 1

Shift for m = 2

Acquisition Depth = $\dfrac{a}{\cos \Theta}$ + C

METHOD AND APPARATUS FOR ENHANCING THE DETECTING AND TRACKING OF MOVING OBJECTS USING ULTRASOUND

STATEMENT REGARDING FEDERALLY SPONSORED RESEARCH OR DEVELOPMENT

Work on this patent application was supported in part by two SBIR contracts: 1) U.S. Navy, Naval Sea Systems Command, Contract #N00024-04-C-4121, and 2) U.S. Army, Army Research Office, Contract Number DAAD19-03-C-0139.

TECHNICAL FIELD

The technical field relates to detecting moving objects using ultrasound technology. One non-limiting application is to detect emboli in the bloodstream.

BACKGROUND

Embolic particles carried by the bloodstream can causes strokes and other circulatory disorders. During surgery emboli may occur when clots form in the blood, air enters into the bloodstream, or tissue fragments break loose or become dislodged. The blood carries the emboli into increasingly smaller arteries until they become lodged and obstruct the flow of blood. The amount of damage that results depends on the size of the emboli, the point in which it lodges in the blood flow, the amount of blood leaking around the emboli, and how blood is supplied by collateral paths around the obstruction. The resulting functional deficit depends in part on the composition of the emboli. For example, air may be reabsorbed in a short time, clots may dissolve, (particularly if blood-thinning drugs are present), while particles composed of plaque and body tissue may not dissolve at all. Therefore, it is important to have non-invasive instrumentation that can accurately detect the presence of emboli, determine their composition, and estimate their size so that appropriate medical management decisions can be made.

Instrumentation for detecting and classifying emboli based on broadband ultrasound is described in U.S. Pat. No. 5,441,051, the disclosure of which is incorporated here by reference. When an emboli passes through an ultrasound beam, the change in acoustic reflectivity causes a reflection which can be detected by an ultrasound receiver. In the '051 patent, the number of embolic events can be counted by monitoring the number of reflected echoes that exceed a predetermined threshold. The '051 patent also describes a method to characterize emboli by composition and size so that an embolus may be classified for example as a gas or a fat particle based on detailed analysis of the echo signal for each embolus.

Before moving objects can be accurately counted and classified, reflected signals from the moving object need to be processed to eliminate reflections from stationary objects that are of less interest. In the blood scanning application, these stationary objects include the blood vessel walls and surrounding tissue. The reflections from surrounding tissue are generally stronger than those from the flowing blood and from the emboli. The strong reflections from stationary objects may be reduced using a moving object indicator (MOI). An MOI temporarily stores one line of echo data and subtracts it from a subsequent line of echo data. Differencing two lines of echo data substantially cancels the stationary object signals leaving the signal reflected from the moving objects, e.g., from the blood flow and the emboli contained therein.

The noise performance of an ultrasonic moving object indicator is a significant issue. One way of improving noise performance is to average multiple lines in such a way that the signal-to-noise ratio is improved. In that case, differences are determined between the averages. The signal-to-noise ratio improves by a factor of the square root of the number of lines averaged when the noise is incoherent and the reflected signal is coherent. Averaging multiple lines results in a waveform that responds slowly to changes. The averaged waveform does not change significantly even when a moving object, e.g., an embolus, passes through the ultrasound beam. The differencing, however, produces a large value when the moving object is present in the ultrasound beam. In addition, the averaging "filter" still leaves significant background noise artifacts.

The inventors realized that the performance of an ultrasonic moving object indicator could be significantly improved. They also recognized that traditional signal-to-noise ratio enhancements are very computationally intensive and thus may often require a specialized or expensive hardware and/or software. In addition, detection of embolic signals based on exceeding a predetermined threshold is not coherent from pulse to pulse, as the amplitude of the return signal often varies with time. Incoherent detection reduces the accuracy of subsequent line tracking and object classification. The echo signal enhancements described below overcome all of these problems.

SUMMARY

An ultrasonic pulse echo apparatus detects a moving object that is moving with respect to its stationary object. An ultrasonic transducer transmits a series of ultrasound pulses in a direction that intersects a path of a moving object. An ultrasound receiver receives a series of lines of echoes from objects in the field of view of the ultrasonic signal. Each echo line corresponds to one of the ultrasonic pulses. A signal processor processes the echo lines from the moving object. The echo lines are time shifted by different amounts and combined at different time shifts to produce different composite lines. The composite line having an optimal signal-to-noise ratio is selected.

The signal processor determines an amplitude of each echo line at a particular range from the ultrasound transducer for each of the different time shifts. In one preferred example embodiment, a median value or an average value of the amplitudes is determined for each time shift. The time shift where the amplitudes have a minimum variance from the median value or average value is selected. The echo envelope lines at the selected time shift are combined to produce the combined echo signal with the optimal signal-to-noise ratio for the particular range. In an alternative example embodiment, the median value of the echo amplitudes is determined at each time shift. The time shift where the echo amplitudes have a maximum of median value is then selected. The echo lines at the selected time shift are combined to produce the combined echo signal with the optimal signal-to-noise ratio for the particular range.

In order to reduce considerably the computational load on the signal processor, an envelope is determined for each of the echo lines. Each echo envelope signal is then sampled at a reduced rate. More specifically, each echo envelope signal is sampled at a reduced rate relative to higher-frequency sampling in the received echo lines required for accurate echo representation. The reduced rate still ensures that at least three sample points are contained within an envelope formed from a one-cycle ultrasonic echo.

Other procedures enhance the signal processing. Echoes from the stationary objects that may be present in each of the echo lines are removed. Filtering of the combined echo signal is also desirable to remove one or more false peaks and to detect the peak corresponding to the moving object echo at each filtered echo signal. Line tracking is then performed to associate the detected peak in the echo line with detected peaks and success of echo lines corresponding to the moving object. Next, a track is determined corresponding to the detected peaks in successive echo lines corresponding to the moving object. The signal processor determines how close a recently-detected peak is to that track, and updates the track by adding that detected peak if it is determined to be sufficiently close. The accuracy of this association process has been improved through a mathematical estimate of the future velocity and position of the moving object based on its current track. The accumulated echoes from each track are used to create a representative echo from the moving object. This representative echo is then used to classify the moving object based on waveform characteristics of the echo.

DETAILED DESCRIPTION

In the following description, for purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details disclosed below. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), field programmable gate arrays, one or more digital signal processors (DSPs), etc.

Figure 1:
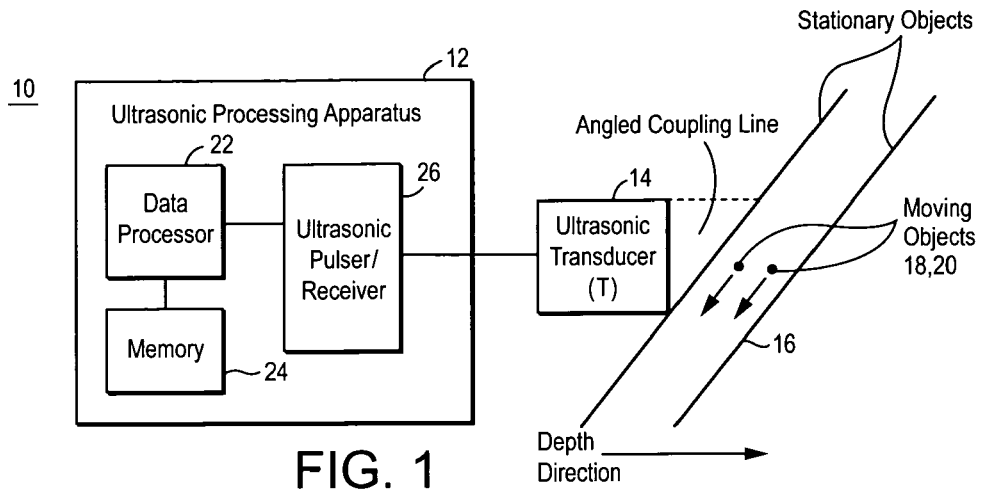
FIG. 1 is a function block diagram illustrating one non-limiting example of an ultrasonic detection apparatus.

FIG. 1 shows a non-limiting example embodiment of a moving object detection system which is indicated by the numeral 10. For purposes of explanation only, and not limitation, the moving object detection apparatus 10 is sometimes described in the context of an emboli detection application. Of course, this technology may be used with other applications. Several other example applications include mechanically scanning structures, parts, or other apparatus for defects, scanning any type of fluid for particles, free hand ultrasound applications, or preferentially enhancing signals from moving fluid through a stationary background.

The moving object detection system 10 includes an ultrasonic processing apparatus 12 that controls an ultrasound transducer 14 positioned so that as moving objects 18 and 20 pass by the ultrasound transducer 14, ultrasonic pulses impinge on the moving objects resulting in reflected echoes that are detected by the ultrasound transducer 14. There are stationary objects 16, shown as a tube or vessel with close and far walls, are also insonified by the ultrasonic pulses and also produce reflected echoes which are detected by the ultrasound transducer 14. In the emboli detection application, the stationary objects correspond to blood vessel walls or walls of other blood transport conduit, and the moving objects correspond to emboli. The term "depth" corresponds to the perpendicular direction away from the ultrasound transducer 14 towards the objects. The ultrasonic processing apparatus includes a data processor 22 coupled to memory 24 and to an ultrasonic pulser/receiver 26.

The ultrasound transducer 14 transmits ultrasound pulses into the body and receives echoes or reflections from within the body. As one non-limiting example, the transducer 14 may be a PZT composite having a quarter wave impedance matching layer to increase the coupling of sound from the transducer 14 into the object objects. The ultrasonic pulser 26 also preferably (but not necessarily) applies fast-rise time step pulses to the transducer 14 which is converted by the transducer 14 into ultrasound signals that reflect off the objects being scanned. One non-limiting example drive pulse has a voltage over 100 volts and a rise time on the order of 15 nanoseconds.

Reflections or echoes from the acoustic impedance changes in the body return to the transducer 14 which converts the reflected acoustic energy into corresponding electronic echo signals. The transducer 20 preferably has a broad bandwidth so that, among other things, it can preserve the polarity of the reflected signals. A plurality of ultrasound transducers may be arranged in an array and operated sequentially to produce adjacent beams that collectively cover larger areas.

Figure 2:
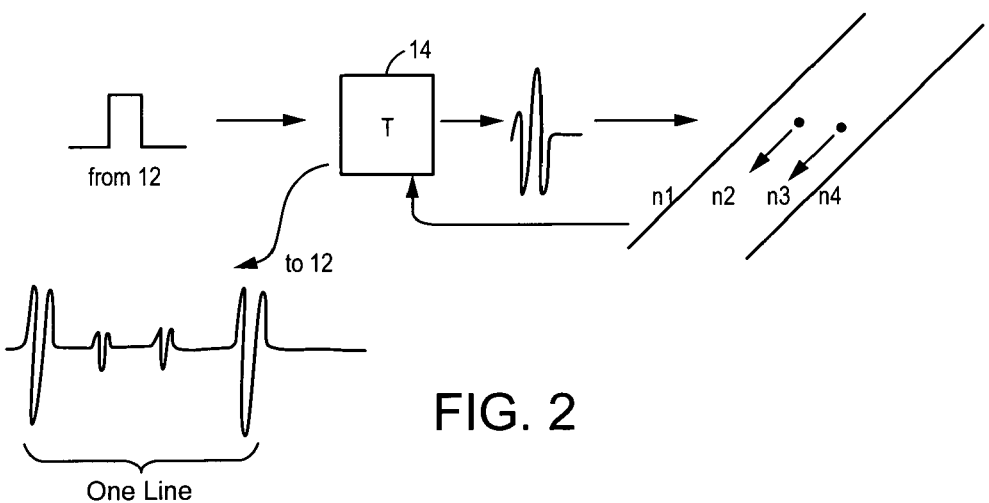
FIG. 2 illustrates an ultrasonic pulse being reflected as RF echoes by stationary and moving objects.

FIG. 2 is a simplified conceptual drawing that illustrates the pulse from the ultrasonic pulser 26 energizing the ultrasonic transducer 14 to generate an ultrasonic quasi-sinusoidal looking wave that impinges on the stationary walls 16 and the moving objects 18 and 20. For each pulse or "ping", each moving and stationary object produces one or more RF echoes. RF echo 1 corresponds to the stationary front wall 16; RF echo 2 corresponds to the moving object 18; RF echo 3 corresponds to the moving object 20; and RF echo 4 corresponds to the stationary back wall 16. All of the echoes that result from one ultrasonic pulse or "ping" are combined together as a single "line". Multiple lines are then processed as described below.

Figure 3:
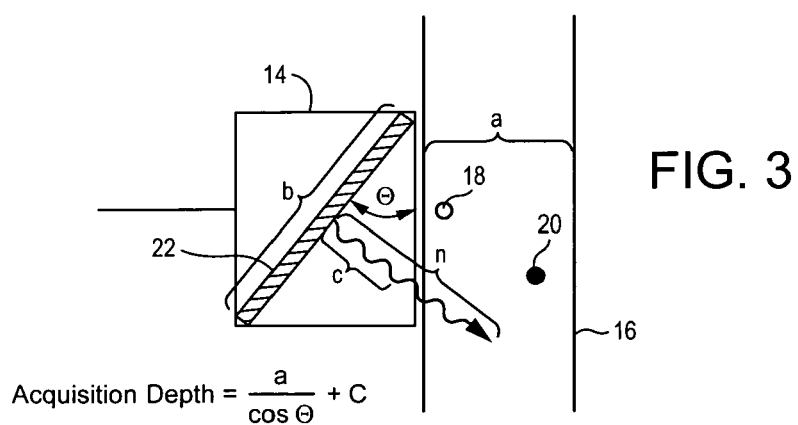
FIG. 3 illustrates the ultrasonic transducer positioned at an angle with respect to the direction of movement of the moving objects and related parameters.

The ultrasound beam is preferably angled with respect to the moving object direction, e.g., the blood flow direction for emboli, so that the effective range from the transducer face to the moving object changes as the moving object passes through the sound beam. This change in the range with respect to time produces a moving object indicator (MOI) shift. FIG. 3 illustrates that angle θ, which may have any suitable value. One non-limiting example value is 30 degrees. Angling the beam makes the moving object shift much larger than that of the surrounding stationary objects, so that the moving object indicator can more easily separate and cancel the echoes from the stationary objects. In addition, an angled beam reduces the strength of echoes from the stationary walls so that dynamic range requirements for detection and signal processing are reduced. The width of the transducer is designated as "b", the width of the tube or blood vessel is "a", and the range "n" is in a direction perpendicular to the surface of the transducer towards the tube or vessel. The range distance from the tube wall to the external surface of the transducer is denoted as "c". The ultrasonic processing apparatus is set to acquire echo lines at a maximum acquisition depth equal to the distance from the transducer face to the back wall of the tube, which equals a/cos θ+c. The distance "c" from the transducer tube wall is shortest at the top of the transducer and longest at the bottom, angled away from the transducer, so that echoes from the tube wall will be spread out over multiple range values n.

The ultrasonic receiver 26 amplifies the small electrical echoes from the transducer 14 to a level suitable for analyzing and processing. The receiver includes amplification, time gain compensation, filtering, and analog-to-digital conversion. Time gain compensation increases gain with time to compensate for the acoustic attenuation experienced as the ultrasound pulse travels deeper in the depth direction shown in FIG. 1, e.g., into the body. Analog-to-digital conversion needs to take place at a rate high enough to preserve the characteristics of the reflected echo signals from the moving objects. As one non-limiting example, with an ultrasound signal centered at 5 MHz, analog-to-digital (A-to-D) conversion rates should be 20 MHz or higher. The A-to-D converter must also have sufficient accuracy to preserve amplitude and polarity information.

The digitized echo outputs are passed to the data processor 22 for subsequent signal processing and stored in the memory 24. Absent the processing enhancements employed by the inventors, very large numbers of samples must be stored and processed for each transmit/receive sequence. At the highest level, the data processor 22 analyzes the electronic echo signals to detect and preferably classify each moving object based on size and composition. If desired, the results of the moving object detection and classification may be displayed or used to produce audible tones, alarms, pre-recorded voice messages, or other signals.

Figure 4:
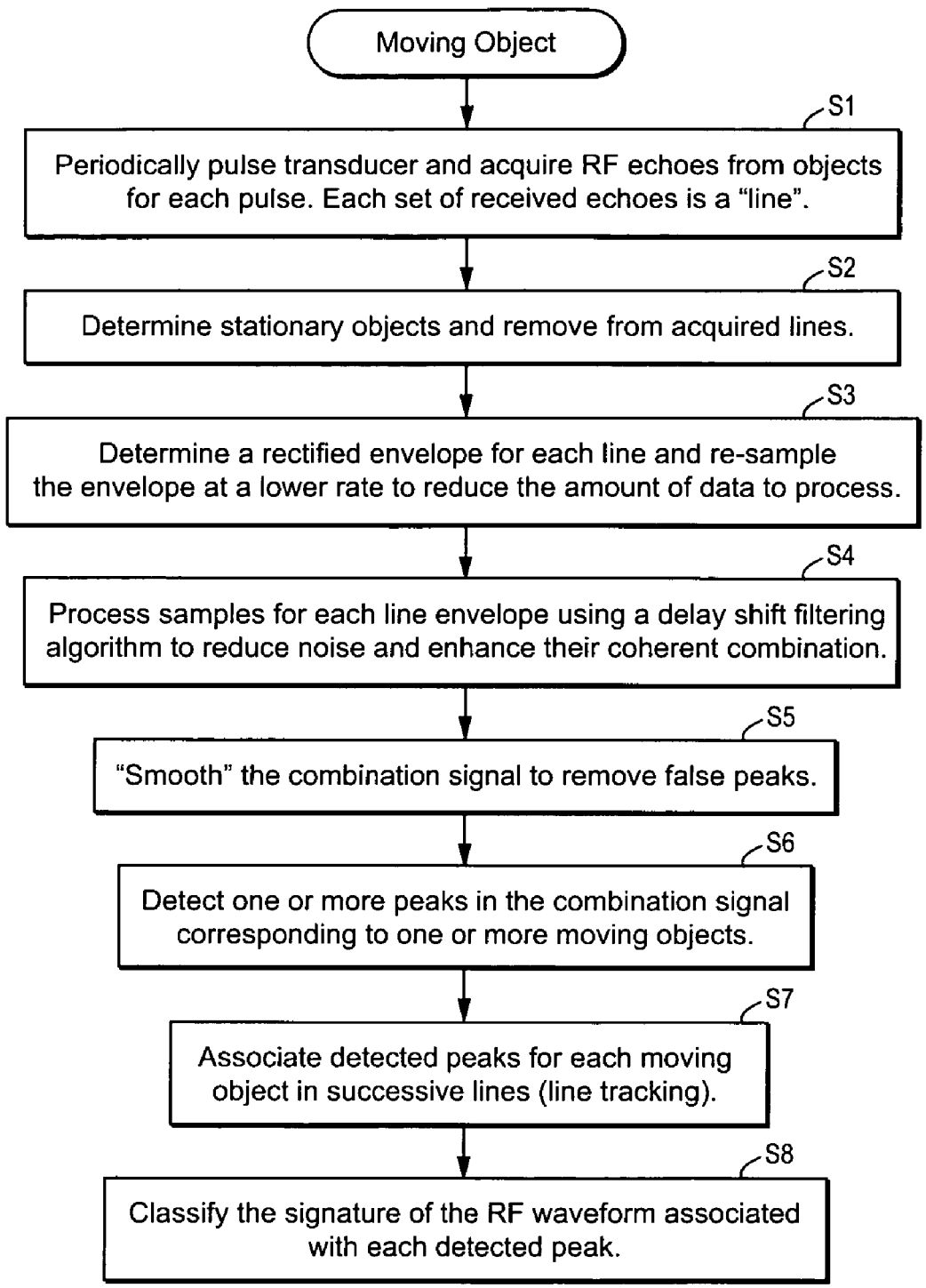
FIG. 4 is a flow chart diagram illustrating non-limiting example steps for detecting a moving object using the ultrasonic detection apparatus shown in FIG. 1.

FIG. 4 illustrates a flowchart labeled "moving object" that outlines non-limiting, example signal processing procedures that may be performed on digitized echo signals. In step S1, the ultrasonic transducer is periodically pulsed to acquire RF echoes from both stationary and moving objects for each pulse. Each set of received echoes per pulse is referred to as a line. The echoes from stationary objects in each line are determined and removed (step S2). A rectified envelope is then determined for each line, and the rectified envelope is re-sampled at a lower sampling rate to reduce the amount of data needed to be processed (step S3). The samples for each line envelope are then processed using a delay shift filtering algorithm to reduce noise and to enhance the coherent combination of multiple envelope lines (step S4). To further improve the inherent line combination process, a further filtering operation is performed to "smooth" the combined signal to remove false peaks (step S5). Then, in step S6, one or more peaks (depending on a number of moving objects) are detected in the combination signal, with each peak detected corresponding to a moving object. The detected peaks in successive lines that corresponds to the same moving object are associated in a process called "line tracking" (step S7). This line tracking, as described below, allows prediction of the future position (range) and velocity of the moving object which allows subsequent analyzing and processing to be focused on a narrower region in terms of position and velocity by excluding all other positions and velocities. The last step describes classifying the "signature" or characteristics of the RF wave form associated with each detected peak (step S8). In some applications, such as emboli detection, classification of the moving object can be very important. For example, the polarity or the phase of the echo may be used to classify an embolus as either gaseous or solid.

Figure 5:
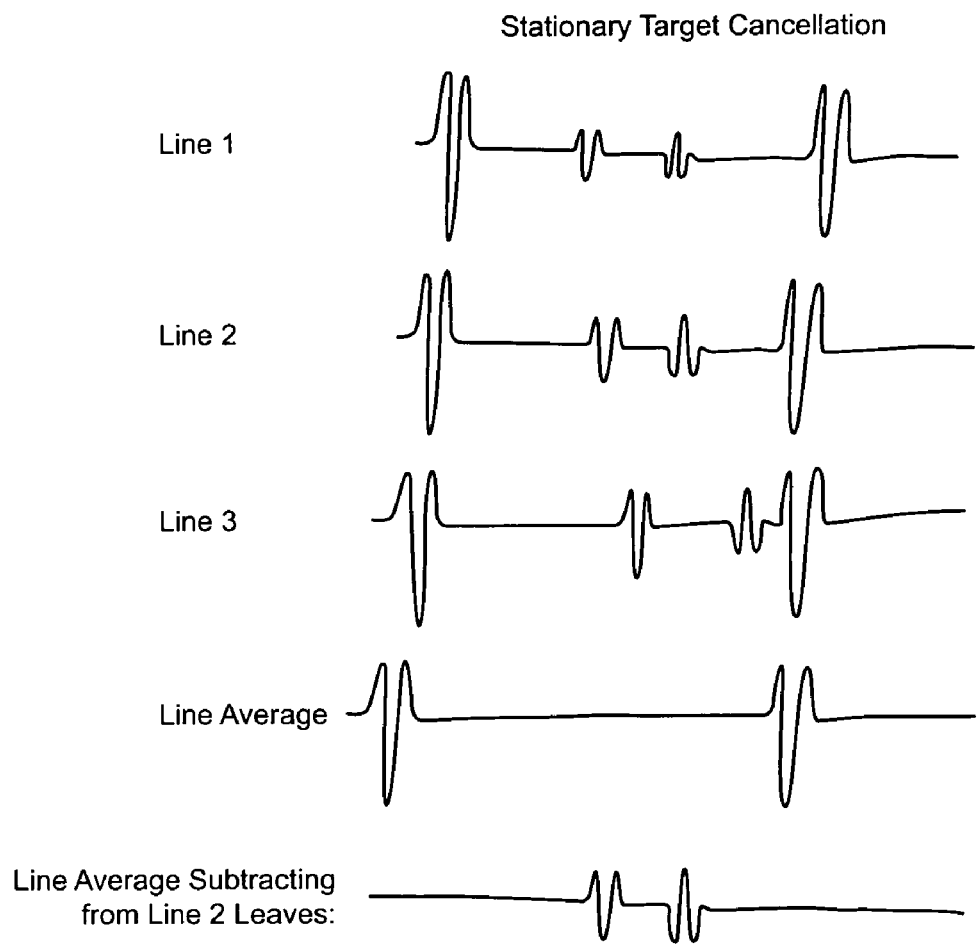
FIG. 5 includes an example to illustrate stationary object cancellation.

A first step of stationary object cancellation (SOC) is illustrated in FIG. 5. In this simplified example, three lines of echoes are added and divided by three to obtain a line average. Then the line average is subtracted from each individual line. The figure shows the result of subtracting the line average from line 2. It is apparent that the large echo waves corresponding to the stationary objects have been removed. But the moving objects do not constructively combine in the line average so they remain in the difference waveform.

In one example implementation, a high-pass filter may be used at each range point "n" taken across multiple lines to remove the large echoes from stationary or slow-moving objects and enhance echoes from faster moving objects. One preferred but still example implementation of an SOC filter H(f) is a moving window average that is subtracted from each line. The moving window average has a sinc frequency response defined by the Fourier transform of a rectangular pulse:

$$H(f)=\sin(M\pi f_p)/(M\pi f_p)$$

where f is the frequency of the ultrasonic pulse, and M is the number of points in the moving average. An example ultrasonic pulse repetition frequency $f_p$ is 1 kHz.

Since the moving average is subtracted from the input line (an RF signal), the frequency response of the filter is:

$$H(f)=1-\sin(M\pi f_p)/(M\pi f_p)$$

For an example of M=9, this filter produces a transfer function with a −3 dB cutoff frequency $f_c$=82 Hz. For M=5, $f_c$=152 Hz and for M=3, $f_c$=252 Hz. The cutoff frequency $f_c$ is converted to a cutoff velocity using the following equation:

$$v_c=d*f_c$$

where d is the distance the object travels during one cycle of the cutoff frequency. This distance is the range value for an ultrasonic echo, which is:

$$d=(\tfrac{1}{2}c*\sin\theta_r)/f_s$$

where c is the speed of sound, $f_s$ is the sampling frequency of the A/D converter, and sin $\theta_r$ is the component of object motion moving toward and perpendicular to the transducer face. For a cutoff frequency of 82 Hz, and an angle of refraction $\theta_r$ of 30°, this translates to a cutoff velocity of 0.065 cm/s. Thus, with M=9, all objects moving at less than 0.065 cm/s will be significantly attenuated relative to faster moving echoes. Depending on the nature of the objects to be tracked and the motion of the background clutter, it may be desirable to adjust the value of M.

Figure 6:
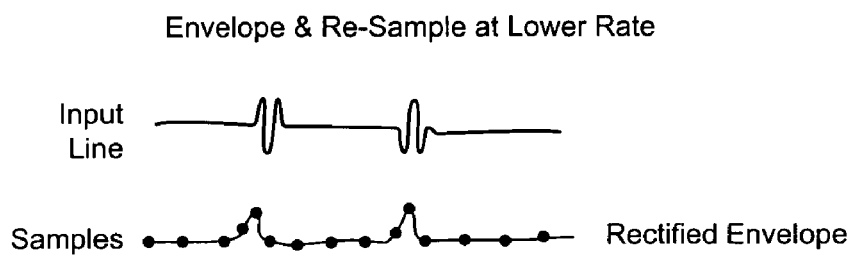
FIG. 6 illustrates an example of determining a rectified envelope of the remaining moving object echo signals and re-sampling the rectified envelope at a reduced sampling rate.
Figure 7:
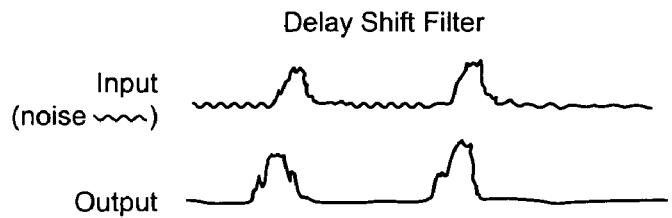
FIG. 7 illustrates the effect of a delay shifting filter.

Detecting moving objects based on their echoes is a multi-step process. Additional processing of the RF line signals is very desirable due to the low signal-to-noise ratio of moving object echoes. First, it is advantageous to convert each RF line signal into a rectified envelope signal, which is a less complicated waveform than the echoes themselves. FIG. 6 shows an example where two echo waveforms are rectified and an envelope determined.

One example way to convert the RF line signal a rectified envelope is using a Hilbert transform operation. The Hilbert transform is implemented by applying a finite impulse response (FIR) filter on the RF line signal data. The FIR filter coefficients may be generated using the following formula:

$$h(n)=(2\pi c/n)\sin^2(n\pi/2)$$

If the ultrasonic transducer has a center frequency of approximately 4 MHz, as one non-limiting example, the filter coefficients need to be adjusted to smooth out the filter ripple. Smoothing may be accomplished by applying a Hanning window to h(n) as follows:

$$y[n]=0.5(1-\cos(2\pi n/N))*(2\pi/n)\sin^2(n\pi/2)$$

In addition to improving the frequency response of the Hilbert transform, the effect of a small DC bias on low-amplitude signals may be reduced or eliminated by applying a negative Hilbert transform to the line signals input for envelope detection:

$$h_{-90}(n)=-h_{+90}(n)$$

The resulting signal is stored in memory and then phase-shifted +90° to produce a second signal, which is in-phase with the original signal but has the DC bias filtered out. The magnitude of this in-phase signal combined with the −90° phase-shifted signal is then used to form the envelope.

A second advantageous signal processing step relates to reducing the amount of data that has to be processed. The inventors determined that considerable computational resources could be conserved without any reduction in processing accuracy by re-sampling the rectified waveform at a much reduced rate. Each echo envelope signal is sampled at a reduced rate relative to higher-frequency sampling in the received echo lines required for accurate echo representation. For instance, a 4 MHz echo should be sampled at 48 MHz to fully represent the echo waveform characteristics. After forming a rectified envelope, much of the frequency content of the echo has been destroyed, and a lower re-sampling rate is adequate to represent the shape of the envelope. Ideally, three points of the envelope are preserved after re-sampling so that the peak of the envelope can be distinguished from the edges. To obtain three samples for each 4 MHz echo, the data must be re-sampled at 3*4 MHz or 12 MHz. This is one-fourth the original sample rate of 48 MHz.

In an example implementation, after forming the rectified envelope, the signal is decimated by a factor of four. Before re-sampling, however, it is preferable to first low pass filter the envelope data to prevent anti-aliasing. Then the data is re-sampled, and every fourth point is output to the delay shift filter. Even at a fairly high resolution, e.g., a one-cycle signal with a center frequency of 4 MHz, a 4:1 decimation provides three sample points per echo, which is sufficient to enable peak detection. The re-sampled rectified envelope in FIG. 6 shows three samples per echo waveform. The four-to-one reduction in sample data provides $4^2=16$ times less computations in subsequent line processing.

The next processing stage is delay shift filtering which enhances the signal-to-noise ratio of the moving object echoes. But before describing the specifics of the delay shift filtering, tests were performed comparing delay shift filtering before forming an envelope and decimating the signal (so that the delay shift filter is performed on all of the acquired echo line data) with filtering the decimated envelope data. In general, delay shift filtering using all the original sample data provided somewhat better signal-to-noise improvements, but at 16 times more computational cost. But at certain signal-to-noise ratios, RF delay shift filtering of the decimated envelope samples actually provided better noise reduction. For most applications, the somewhat improved sensitivity does not outweight the significantly reduced computational cost achieved with filtering just the decimated envelope samples.

Delay shift filtering shifts in time the echoes corresponding to the same moving object by different delay shift amounts in order to determine the optimal shift value that allows the same object echoes to be evaluated over a coherent track. The echoes of faster moving objects require more shifting than the echoes of slower moving objects.

For T successive echo lines, where X is the echo amplitude when the moving object is at range n from the transducer, and t is the time at which the line was acquired, the range of each line is delay-shifted in time according to the following formula:

$$Temp[m][t][n]=X[t][n-d]$$

where Temp refers to an array in memory for storing a series of lines being processed, m is a parameter associated with the amount d by which the range n has been shifted, and the shift amount d depends on m, t and T as follows:

$$d=\frac{1}{2}*[mt(T-1)]$$

The memory array Temp[m][t][n] stores the time-shifted values X[t][n−d], which are then evaluated statistically to produce another temporary memory array Temp2[m][n].

The number of delays used in the delay shift filtering is determined by the range of possible velocities of the moving object. As one example related to emboli carried in the blood stream, a range of velocities of the emboli might be 0.1 m/s to 1 m/s. The formula below converts these velocities into a slope given in units of samples per ping or line:

$$m = \frac{\Delta range}{\Delta ping} = \frac{2t_{ping}f_s v_f \sin\theta}{c}$$

where $t_{ping}$ is the pulse repetition period, c is the speed of sound in tissue (1540 m/s), $f_s$ is the decimated sample rate of 12 MHz, $v_f$ is the flow velocity of the emboli, and θ is the transducer angle relative to the flow direction. For objects moving over a range from 0.1 m/s to 1 m/s, the range of delay shifts "m" is 0.8 samples/ping to 8 samples/ping. The lower limit is rounded down to zero so that nine delay shifts are needed for the delay shift filter, ranging from 0 to 8 samples/ping or line. Finer resolution shifting may also be used, but finer resolution may not translate into greater detector sensitivity.

The value of the time shift m that provides optimal enhancement of the echo signal-to-noise ratio is then chosen to produce a new, noise-reduced line Y[n] that is a composite of the T lines X[t][n] at that selected delay shift. Three methods for determining the delay shift for the optional composite line Y[n] with statistically reduced noise as compared to each of the lines X[t][n] are described:

Averaging: Compute an average value of the T lines at delay m (which can be thought of as a slope of sorts) and range n, and choose Y[n]=max {Temp2[m][n]}.

Find the Median: Sort the T lines at slope m and range n lowest to highest, and set Temp2[m][n]=Temp[m][(T+1)/2][n]. Choose Y[n]=max {Temp2[m][n]}

Determine the Minimum Variance: After computing Temp2[m][n] using either a mean or a median value, compute the variance about the mean (or median) using the formula var[m][n]=Σ(Temp2[m][n]−Temp[m][t][n])². Choose Y[n] as the value of Temp2[m][n] that gives the minimum variance.

Both the enhanced line Y[n] and a corresponding array M[n] of the shifted values used to obtain Y[n] may be stored in memory. The latter data gives some indication of how fast a object is moving, since the time shift m that reduces noise the most corresponds to object motion. This array M[n] data may be advantageously used in the line tracking processing described below.

Figure 8A:
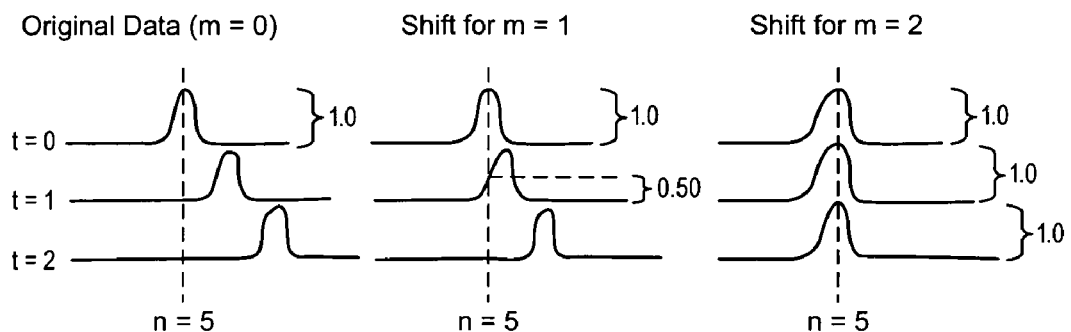
FIGS. 8A and 8B illustrate delay shifting examples.

FIG. 8A provides a simplified illustration for three lines or "pings", i.e., T=3, and three time shift values m=0, m=1, and m=2. The illustration shows shifts for lines all at the same depth n=5. But in application, the same computations would be made for all values of n. For no shift with m=0, the three line echoes do not overlap, and only the first line echo has a non-zero amplitude at the depth n=5. For a small delay shift of m=1, the second line echo overlaps the first line echo. For a larger delay shift of m=3, the second and third line echoes line up with the first line echo.

The following table illustrates how the different delay shifts may be statistically combined to achieve enhanced signal-to-noise ratio for a composite line representing the three lines as compared to any one of the three individual lines. The three statistical combinations of averaging, finding the median, and determining a minimum variance are employed. In this example, the variance is computed against the median, but it could also be computed against the average.

| Original Data m = 0 | m = 1 | m = 2 |
|---|---|---|
| Temp [0] [0] [5] = 1 | Temp [1] [0] [5] = 1 | Temp [2] [0] [5] = 1 |
| Temp [0] [1] [5] = 0 | Temp [1] [1] [5] = ½ | Temp [2] [1] [5] = 1 |
| Temp [0] [2] [5] = 0 | Temp [1] [2] [5] = 0 | Temp [2] [2] [5] = 1 |

|  | m = 0 | m = 1 | m = 2 |
|---|---|---|---|
| Average: | Temp 2 [0] [5] = ⅓ | Temp 2 [1] [5] = ½ | Temp 2 [2] [5] = 1 |
| Median: | Temp 2 [0] [5] = 0 | Temp 2 [1] [5] = ½ | Temp 2 [2] [5] = 1 |
| Median Variance: | Var [0] [5] = 1 | Var [1] [5] = ½ | Var [2] [5] = 0 |

The delay selected for the optimal enhanced output Y[n] using each of these statistical composite approaches is:

| Average: | Y [5] = max {Temp 2 [m] [5]} = 1; M [5] = 2 |
|---|---|
| Median: | Y [5] = max {Temp 2 [m] [5]} = 1; M [5] = 2 |
| Median Variance: | Y [5] = Temp 2 [2] [5] = 1; M [5] = 2, since Var [m] [5] is minimum for m = 2. |

The goal is to determine which delay shift will result in the optimal combination of the line echoes. From the waveforms in FIG. 8A, it is straightforward to visually identify that delay shift m=2 is the optimal shift because the line echoes are aligned. But this needs to be implemented so that a computer algorithm can automatically make this determination. For m=0, the average of 1, 0, and 0 is ⅓; the median is 0, and the median variance i.e., how much each line shift value varies from the median line shift value, is 1. As shown above, all three statistical combining techniques select m=2 as the optimal shift at which to combine the line echoes to achieve the most enhancement of the signal relative to the noise.

But not all three statistical combining techniques perform as well in different situations. The use of an average value, however, tends to also increase the background noise level, as some delay shifts may intersect a detected signal at one point but consist mostly of noise. The inventors refer to this effect as "shadowing" because the noise clutter tends to follow a detected signal like a shadow. Using the median composite selection approach can reduce shadowing by reducing the effect of outlier points during delay shift filtering. But the minimum covariance approach is even better.

Figure 8B:
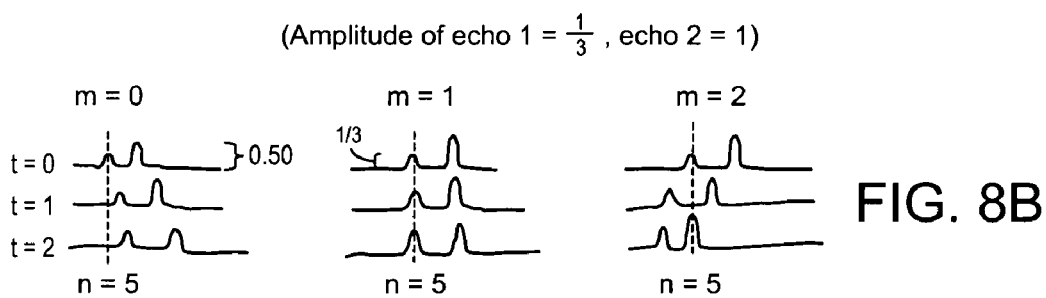
Figure 9:
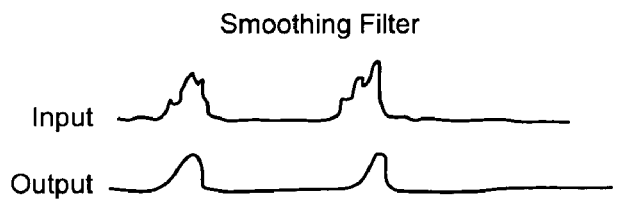
FIG. 9 illustrates the effect of a waveform smoothing filter.
Figure 10:
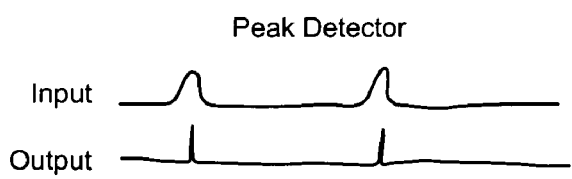
FIG. 10 illustrates a peak detection example.
Figure 11:
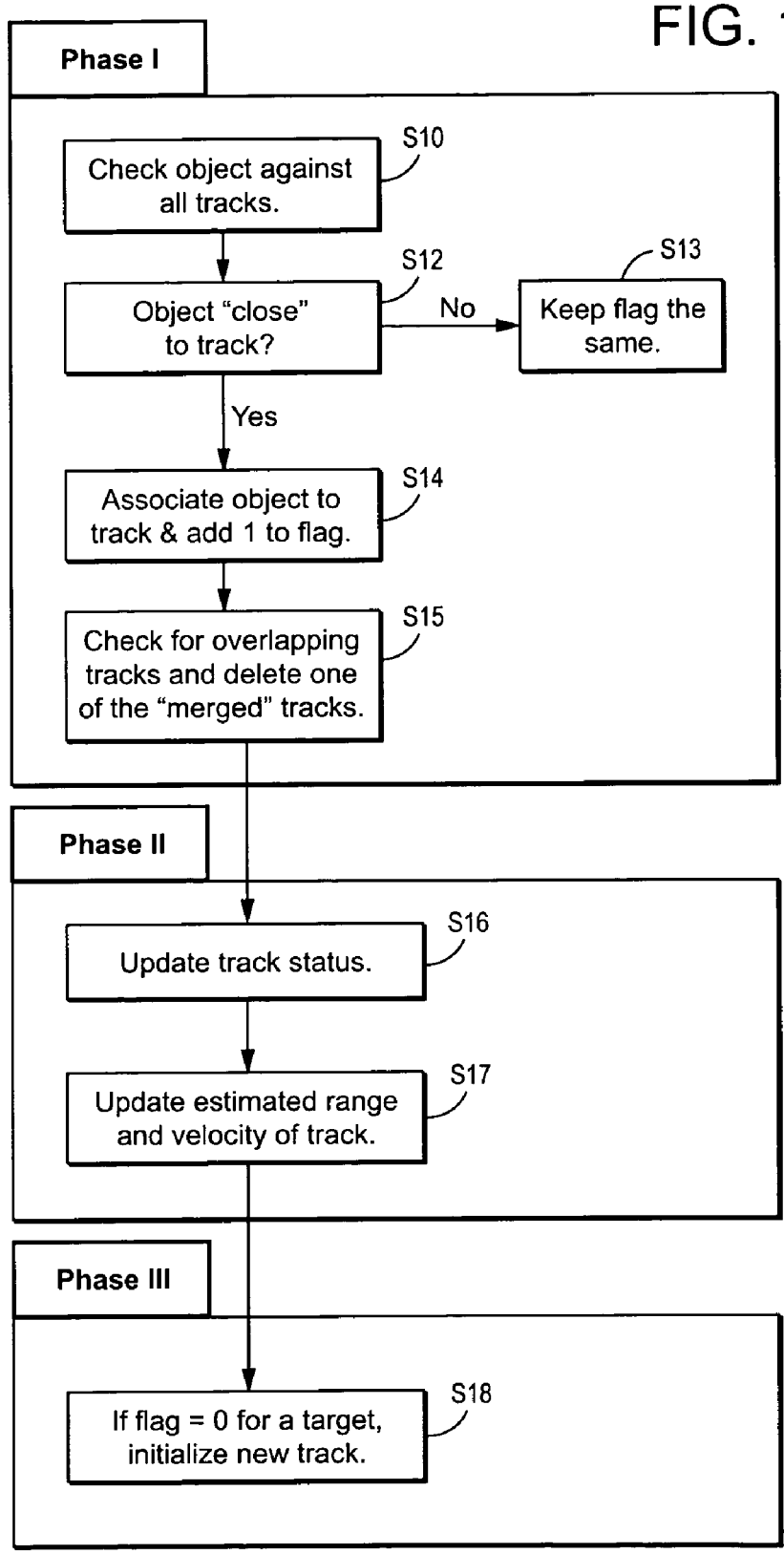
FIG. 11 is a flow chart diagram illustrating non-limiting example steps for implementing line tracking.

FIG. 8B helps illustrate how the minimum covariance delay shift selection produces a more optimal echo composite signal when clutter (larger amplitude curves) is present near the echoes (smaller amplitude curves). Again, three lines are statistically analyzed at range n=5 for three time delay shifts of m=0, m=1, and m=2. Visually, it is apparent that the line echo pulses best line up for m=1, which means that the delay shift filter algorithm should select the composite signal for m=1. But as the following table demonstrates, the averaging approach wrongly selects shift m=2 because the overlapping large noise amplitude—rather than the desired echo for that line—generates the largest average of the three. On the other hand, the minimum variance delay shift selection approach determines that the minimum variance of 1 from the median value of ⅓ occurs at m=1. The median approach is ambiguous because both delays m=1 and m=2 result in the same median amplitude of ⅓. So in the presence of significant clutter, the minimum variance delay shift selection approach is optimal.

| m = 0 | m = 1 | m = 2 |
|---|---|---|
| Temp [0] [0] [5] = ⅓ | Temp [1] [0] [5] = ⅓ | Temp [2] [0] [5] = ⅓ |
| Temp [0] [1] [5] = 0 | Temp [1] [1] [5] = ⅓ | Temp [2] [1] [5] = 0 |
| Temp [0] [2] [5] = 0 | Temp [1] [2] [5] = ⅓ | Temp [2] [2] [5] = 1 |

|  | m = 0 | m = 1 | m = 2 |
|---|---|---|---|
| Average: | Temp 2 [0] [5] = ⅑ | Temp [1] [5] = ⅓ | Temp 2 [2] [5] = 4/9 |
| Median: | Temp 2 [0] [5] = 0 | Temp 2 [1] [5] = ⅓ | Temp 2 [2] [5] = ⅓ |
| Median Variance: | Var [0] [5] = ⅓ | Var [0] [5] = 0 | Var [2] [5] = 0.75 |

| Output Y [n] | |
|---|---|
| Average: | Y [5] = max {Temp 2 [m] [5]} = 4/9; M [5] = 2 |
| Median: | Y [5] = max {Temp 2 [m] [5]} = ⅓; M [5] = 1 (or 2) |
| Median Variance: | Y [5] = Temp 2 [1] [5] = ⅓; M[5] = 1, since var [m] [5] is a minimum for m = 1. |

The maximum median filter is somewhat more sensitive than the minimum variance filter, but at the cost of introducing additional noise. Thus, the maximum median filter is more likely to produce false positive readings, particularly in cluttered environments, but more likely to detect weak signals. An additional advantage of the minimum variance filter is that the detected position is more coherent than with the maximum median filter, resulting in stronger RF signatures when the signal is averaged along a track.

The inventors performed various tests using simulated data to compare the performance of the maximum median and minimum variance filter approaches. At a signal-to-noise ratio (SNR) of 1.8 dB, the maximum median filter was swamped by noise, making detection very difficult, while the minimum variance filter did a better job of noise reduction so that the echo signal track could be separated from the noise. At a higher SNR of 3.3 dB, the maximum median filter performed better than the minimum variance filter. The maximum median filter did a better job of enhancing the composite signal so that the track is stronger than in the minimum variance filter.

Nonetheless, the minimum variance filter was determined to provide better performance than the maximum median filter in cluttered environments. The sensitivity advantage of the maximum median filter may be compensated for by hardware improvements that increase the signal-to-noise ratio of the input data. Significantly, the minimum variance filter is considerably less computationally intensive than the maximum median filter, since the minimum variance filter computations perform only about half (e.g., 5 lines of data are needed in the test example) of the number of computations required for the maximum median filter (e.g., 9 or 11 needed in the test example). This computational reduction of one half coupled with computational reduction of one sixteenth achieved in the lower sampling rate of the echo envelope results in an overall computation reduction of 1/32 when the minimum variance approach is used. No loss in accuracy was observed, even though the number of computations was reduced 32 times.

Tests were also performed to compare performing delay shift filtering before forming an envelope and decimating the signal (so that the delay shift filtering is performed on RF data) with the use of delay shift filtering after forming an envelope. Delay shift filtering on the RF data provided somewhat better signal-to-noise ratio, but at 16 times more computational cost. With a SNR of 1.9 dB, an RF delay shift filtering performed on RF data provided better noise reduction than the delay shift filtering on the rectified envelope, but the signal level was higher for delay shift filtering on the rectified envelope. Ultimately, the RF delay shift filtering performed on RF data did not increase the sensitivity of the detector enough to justify the extra computational cost.

If a minimum variance condition is used to select delay shifts instead of a maximum signal condition used in the average and median value approaches, it may be necessary to adjust the length of the delay shift filter. For the maximum signal condition, the best results are obtained when the median or average value is calculated over 12 or more lines because signal-to-noise improves with $\sqrt{N}$, where N is the number of lines over which the delay shift filter is implemented. Thus, it is desirable to make N as large as bandwidth and computational resources permit. For the minimum variance conditions, the best results are obtained when the median or average value is calculated over fewer lines, as it becomes progressively more difficult to find a coherent path as N increases. As a result, signal-to-noise has been found to decrease for large values of N. In one non-limiting test related to emboli detection, the best results for the minimum variance condition were achieved with n=5.

After delay shift filtering to enhance signal-to-noise ratio of the echoes in a composite line, the next step is to filter the composite line to smooth the echo wave shapes. Even with delay shift filtering enhancement, there is still inherent system noise. Because the delay shifts are only calculated over integer values, the echo envelope peaks tend to decorrelate. That means that noise rides on top of an echo envelope peak, so that a peak detector based on finding local maxima will output a cluster of detected events around a global maximum that passes a minimum threshold test.

To reduce detection of false peaks, the composite lines are processed by a smoothing filter, e.g., a Gaussian smoothing filter. A Gaussian smoothing function g[n] may be derived via the following function:

$$g[n] = \frac{1}{2\pi\sigma} e^{-n^2/2\sigma^2}$$

Most common Gaussian smoothing functions use a 5-tap filter with σ=1.4.

The next step is detecting the peaks of the echoes. Peak detection provides more reliable estimation of the range of an object than threshold detectors because they detect a common feature within the echo envelope—the peak value—that does not vary in range as the amplitude of the signal changes. One example of a peak detector implementation is based on a quadratic curve fit of the data over a moving N-point window. Although accurate and reliable, this implementation is computationally intensive. An alternative is a peak detection algorithm based on a finite difference operator. A central difference operator is preferred because it has the same computational requirements as a forward or backward difference operator, but is less sensitive to noise.

The central difference operator differentiates (the derivative operation is represented as d_) the output Y of the Gaussian smoothing operator as follows:

$$d\_Y_n = Y_{n+1} - Y_{n-1};$$

A peak is defined at any point where $d\_Y_n > 0$ and $d\_Y_{n+1} \leq 0$, and where $Y_n$ exceeds a threshold value defined by the background noise characteristics of the ultrasonic system. Testing indicates that the central difference operator detects peaks equivalently to the quadratic curve fit so long as the detection threshold is raised by approximately 25%. The higher threshold is required because the quadratic curve returns an estimated peak that is lower than the peak in the detected data, while the central difference operator returns the actual peak value.

After peak detection, line tracking is performed to associate detected object echoes along the moving trajectory of that object so that multiple detections from a single object are not counted more than once. The line tracker also provides additional filtering of spurious noise events and provides a convenient way to acquire an RF signature of an object echo. As described below, the RF signature may then be used to classify the object by size, composition, or other characteristics, if desired.

Figure 12:
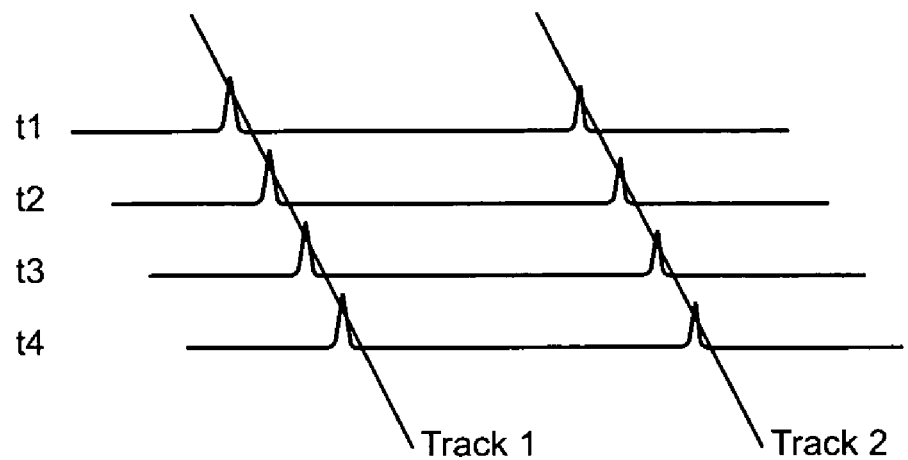
FIG. 12 illustrates line tracking.

For each line of echo data, the line tracking algorithm associates detected echo peaks with existing object tracks and maintains the data in a track table in memory. As shown in FIG. 12, the example line tracking algorithm operates in three phases I, II, and III. In phase I, detected events (i.e., objects) from one cycle are checked against all tracks (step S10) and associated with one or more deferred or active tracks. The detected event is associated with a track if the range of this object is "close" to the estimated range in the track table (step S12), and if the measured delay shift or "slope" (obtained from the delay shift filter output) is "close" to the estimated velocity. If not, a current line tracking flag value is maintained (step S13). Closeness is defined by an error bar around the difference between the estimated range and measured range and an error bar between the measured delay shift/slope and the estimated velocity. For range, a small error bar or +/−2 range values may be appropriate, as large error bars may create false tracks. For velocity, a larger error bar of +/−3 may be better as smaller errors tend to create false negatives. Of course, these are examples only, and other error bar values may be used. In the case that multiple detected events/objects are within both error bars, the event closest to the estimated position is associated with the track. When an object peak is associated with a track, the flag is incremented by 1 (step S14). As part of the association process, range and magnitude data for the peak are added to the track table, and the original RF echo data, obtained at the output of the stationary object canceller, is added to the accumulated echo stored within the track table. This accumulated echo signature is used later for classification of the moving object. A check is made for overlapping tracks, and if overlap is detected, the shorter of the overlapping tracks is terminated (prior to updating track state in Phase II) or deleted, depending on the length of the track (step S15).

In Phase II, the track state (deferred, active, or terminated) is updated, the estimated position and velocity of the moving object is updated, and old events are rotated out of the track table. The track state may be updated (step S16) using the following non-limiting example procedures:

1. If the length is <10, then the track state is deferred.
2. If the track length is >10 and there have been 6 detections during the last 10 lines, then the track state is active.
3. If the track length is >10 and there have not been 6 detections during the last 10 lines, then the track state is terminated.

The future position/range estimate X_est for the moving object and the future velocity estimate V_est for the moving object are estimated for the next cycle based on the current track for that moving object (step S17). In one non-limiting example, that estimation may be determined using a Kalman filter as follows:

$$V\_est = v\_est + h^*(\text{current position} - \text{estimated position } (x\_est)), \text{ where}$$

$$X\_est = x\_est + v\_est + g^*(\text{current position} - \text{estimated position } (x\_est)).$$

The factors g and h are smoothing factors that reduce the jitter in the estimate based on measurement error. The choice of g and h depends on how much the object's velocity is expected to change from line to line, and what the measurement error is in determining the range of the object.

These position and velocity estimates from the line tracker can be useful in predicting where the moving object will be in the next line. By comparing estimated positions and velocities with measured positions and velocities in the next line, it is possible to accurately determine whether a detected object should be associated with a track. If the detected range and velocity are close to the estimated values for any existing track, then the detected event is added to that track. If not, the detected event is used to start a new track. Accurate estimation of future detections provides for more accurate tracking of moving objects in a cluttered environment when multiple objects are detected within each line of echo data.

In Phase III, peaks that were not associated with tracks in Phase I are used to initiate new tracks (step S18). To initialize the velocity estimate, the delay shift data from the delay shift filter is use to give an initial V_est and X_est.

Figure 13:
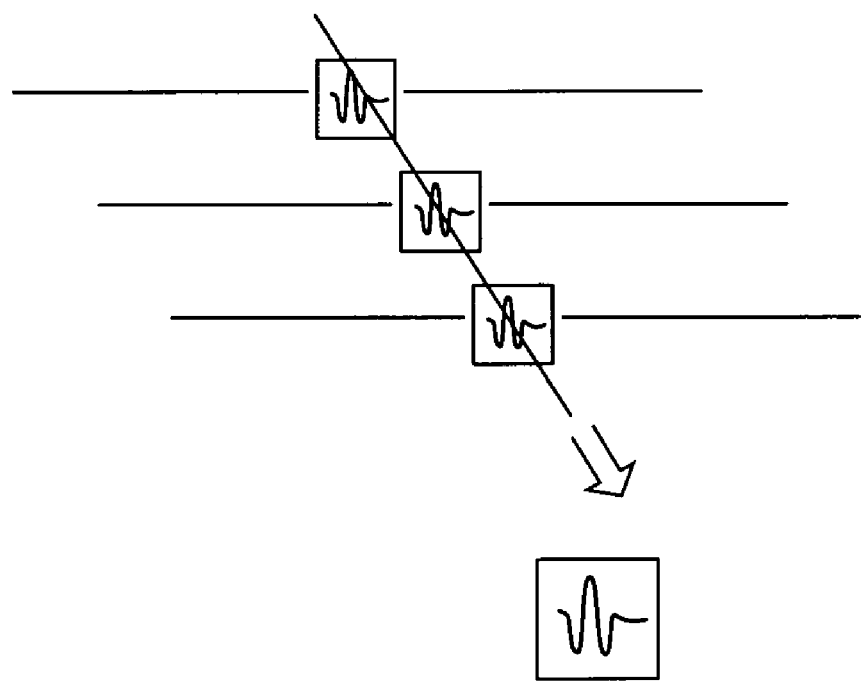
FIG. 13 represents conceptually the accumulation of echoes from a line track and the resulting echo waveform used for signal classification.

The next procedure is signature classification. Before counting a track output as an object, e.g., an embolus, the track data is used to pull an RF signature from stationary object cancellation (SOC) data in memory. These RF signatures are averaged along the track, and the signature may then be analyzed to determine if the track consists of coherent—and therefore valid—RF signatures or if it consists primarily of noise. This is illustrated conceptually in FIG. 13. A threshold detector, in which the signature passes the test if the signature passes a certain threshold, can be used to measure the degree of coherence. Further classification of the signal may be possible through detailed analysis of the time-domain signature, by performing a fast Fourier transform on the signal to analyze its spectral content, or any number of other signal characterization techniques. Other classification methods may be employed such as those described in U.S. Pat. No. 5,441,051.

By forming an envelope of the moving object echoes and re-sampling the envelope at a much reduced sampling rate, the computational requirements of the delay shifting filter were reduced by a factor of 16 without sacrificing performance. In addition, the use of a minimum variance condition to select the best output of the slope filter reduces noise artifacts that were present in the previous version and further reduces computational requirements. The use of a peak detection algorithm for selecting objects to track instead of a threshold detector permits setting the threshold based on the system noise level without subjecting the system to spurious detections that would overload the line tracker. In addition, detecting the signal at the same phase point results in coherent detection from line to line. In contrast, when signals are detected after exceeding a predetermined threshold, the phase point of detection varies with the amplitude of the detected signal. Incoherent detection reduces the accuracy of subsequent line tracking and object classification.

Although various embodiments have been shown and described in detail, the claims are not limited to any particular embodiment or example. None of the above description should be read as implying that any particular element, step, range, or function is essential such that it must be included in the claims scope. The scope of patented subject matter is defined only by the claims. The extent of legal protection is defined by the words recited in the allowed claims and their equivalents. No claim is intended to invoke paragraph 6 of 35 USC §112 unless the words "means for" are used.

The invention claimed is:

1. An ultrasonic pulse echo apparatus for detecting an object that is moving with respect to a stationary object, comprising:
   an ultrasound transducer for transmitting a series of ultrasound pulses in a direction that intersects a path of the moving object;
   an ultrasound receiver for receiving multiple lines of echoes from the objects in the field of view of the ultrasonic signal, each echo line corresponding to one of the ultrasonic pulses; and
   a signal processor for determining an envelope of each of the echo lines, time shifting the echo envelope lines different amounts, and preferentially enhancing the echoes from moving objects by combining the echo envelope lines at different time shifts and selecting one of the combined echo envelope lines with an optimal signal-to-noise ratio.

2. The apparatus in claim 1, wherein the time shifting aligns the echoes in the echo envelope lines, and wherein the signal processor is configured to determine an amplitude of each echo envelope at a particular range from the ultrasound transducer for each of the different time shifts.

3. The apparatus in claim 2, wherein the signal processor is configured to:
determine a median value or an average value of the envelope amplitudes at each time shift,
select the time shift where the envelope amplitudes have a minimum variance from the median value or average value, and
combine the echo envelope lines at the selected time shift to produce the combined echo envelope signal with the optimal signal-to-noise ratio for the particular range.

4. The apparatus in claim 2, wherein the signal processor is configured to:
determine a median value of the echo envelope amplitudes at each time shift,
select the time shift where the echo envelope amplitudes have a maximum median value, and
combine the echo envelope lines at the selected time shift to produce the combined echo envelope signal with the optimal signal-to-noise ratio for the particular range.

5. The apparatus in claim 1, wherein the signal processor is configured to sample each echo envelope signal at a reduced rate relative to higher-frequency sampling in the received echo lines required for accurate echo representation.

6. The apparatus in claim 5, wherein the reduced rate ensures that at least three sample points are contained within an envelope formed from a one-cycle ultrasonic echo.

7. The apparatus in claim 1, wherein the processor is configured to determine an envelope of each of the echo lines using a Hilbert transform and determine an envelope of each of the echo lines and remove a DC bias using a negative Hilbert transform.

8. The apparatus in claim 1, wherein the processor is configured to remove echoes associated with stationary objects that may be present in each of the echo lines.

9. The apparatus in claim 1, wherein the processor is configured to filter the combined echo envelope signal to remove one or more false peaks and to detect a peak corresponding to the moving object echo in each filtered echo envelope signal.

10. The apparatus in claim 9, wherein the processor is configured to associate the detected peak in the echo envelope line with detected peaks in successive echo envelope lines corresponding to the moving object.

11. The apparatus in claim 10, wherein the processor is configured to:
determine a track corresponding to the detected peaks in the successive echo envelope lines corresponding to the moving object,
determine how close a recently detected peak is to the track, and
update the track by adding the detected peak to the track if the recently detected peak is within a predetermined distance to the track.

12. The apparatus in claim 11, wherein the processor is configured to:
estimate a velocity and a position of the moving object based on the track.

13. The apparatus in claim 1, wherein the processor is configured to classify the moving object based on waveform characteristics of the received echoes in each line.

14. A method for detecting an object that is moving with respect to a stationary object using ultrasonic pulse echo apparatus, comprising:
using an ultrasound transmitter to transmit a series of ultrasound pulses in a direction that intersects a path of the moving object;
using an ultrasound receiver to receive multiple lines of echoes from the objects in the field of view of the ultrasonic signal, each echo line corresponding to one of the ultrasonic pulses; and
using a processor to:
determining an envelope of each of the echo lines,
time shifting the echo lines different amounts, and
preferentially enhancing the echoes from moving objects by combining the echo envelope lines at different time shifts and selecting one of the combined echo envelope lines with an optimal signal-to-noise ratio.

15. The method in claim 14, wherein the time shifting aligns the echoes in the echo envelope lines, the method further comprising: determining an amplitude of each echo envelope at a particular range relative to the ultrasonic pulse echo apparatus for each of the different time shifts.

16. The method in claim 15, further comprising:
determining a median value or an average value of the envelope amplitudes at each time shift,
selecting the time shift where the envelope amplitudes have a minimum variance from the median value or average value, and
combining the echo envelope lines at the selected time shift to produce the combined echo envelope signal with the optimal signal-to-noise ratio for the particular range.

17. The method in claim 15, further comprising:
determining a median value of the echo envelope amplitudes at each time shift,
selecting the time shift where the echo envelope amplitudes have a maximum median value, and
combining the echo envelope lines at the selected time shift to produce the combined echo envelope signal with the optimal signal-to-noise ratio for the particular range.

18. The method in claim 15, further comprising: sampling each echo envelope signal at a reduced rate relative to higher-frequency sampling in the received echo lines required for accurate echo representation.

19. The method in claim 18, further comprising: setting the reduced rate to ensure that at least three sample points are contained within an envelope formed from a one-cycle ultrasonic echo.

20. The method in claim 14, further comprising:
determining an envelope of each of the echo lines using a Hilbert transform,
determining an envelope of each of the echo lines, and
removing a DC bias using a negative Hilbert transform.

21. The method in claim 14, further comprising:
removing echoes associated with stationary objects that may be present in each of the echo lines.

22. The method in claim 14, further comprising:
filtering the combined echo envelope signal to remove one or more false peaks, and
detecting a peak corresponding to the moving object echo in each filtered echo envelope signal.

23. The method in claim 22, further comprising:
associating the detected peak in the echo envelope line with detected peaks in successive echo envelope lines corresponding to the moving object.

24. The method in claim 23, further comprising:
determining a track corresponding to the detected peaks in the successive echo envelope lines corresponding to the moving object, determining how close a recently detected peak is to the track, and updating the track by adding the detected peak to the track if the recently detected peak is within a minimum distance threshold to the track.

25. The method in claim 24, further comprising:

estimating a velocity and a position of the moving object based on the track.

26. The method in claim 14, further comprising:

classifying the moving object based on waveform characteristics of the received echoes in each line.

27. An ultrasonic pulse echo apparatus for detecting an object that is moving with respect to a stationary object and subjected to a sequence of ultrasound pulses that intersect a path of the moving object, comprising:

an ultrasound receiver for receiving multiple lines of echoes from the objects in the field of view of the ultrasonic signal, each echo line corresponding to one of the ultrasonic pulses; and processing circuitry for preferentially enhancing the echoes from moving objects and configured to:

time shift the echo lines different amounts, determine an amplitude of each echo line at a particular range from the ultrasound pulse echo apparatus for different time shifts, combine the echo lines at different time shifts, determine a median value or an average value of the echo lines amplitudes at different time shifts, and select the time shift where the echo amplitudes have a minimum variance from the median value or average value.

28. The apparatus in claim 27, wherein the processing circuitry is configured to sample each echo signal at a reduced rate relative to higher-frequency sampling in the received echo lines required for accurate echo representation.

29. The apparatus in claim 28, wherein the reduced rate ensures that at least three sample points for a one-cycle ultrasonic echo.

30. An ultrasonic pulse echo apparatus for detecting an object that is moving with respect to a stationary object and subjected to a sequence of ultrasound pulses that intersect a path of the moving object, comprising:

an ultrasound receiver for receiving multiple lines of echoes from the objects in the field of view of the ultrasonic signal, each echo line corresponding to one of the ultrasonic pulses; and processing circuitry for preferentially enhancing the echoes from moving objects, determining a track corresponding to detected echoes in successive echo lines corresponding to the moving object, determining how close a recently detected echo is to the track, and updating the track by adding the detected echo to the track if the recently detected echo is within a minimum distance threshold to the track.

31. The apparatus in claim 30, wherein the processor is configured to estimate a velocity and a position of the moving object based on the track.

* * * * *